United States Patent [19]  [11] 4,193,929
Hildon et al.  [45] Mar. 18, 1980

[54] EPOXIDATION

[75] Inventors: Anthony M. Hildon, Tattenhall; Peter F. Greenhalgh, Widnes, both of England

[73] Assignee: Propylox a Societe Anonyme, Brussels, Belgium

[21] Appl. No.: 839,887

[22] Filed: Oct. 6, 1977

[30] Foreign Application Priority Data

Oct. 26, 1976 [GB] United Kingdom ............... 44452/76

[51] Int. Cl.$^2$ ........................................... C07D 301/14
[52] U.S. Cl. ............................................... 260/348.25
[58] Field of Search .................................. 260/348.25

[56] References Cited
FOREIGN PATENT DOCUMENTS 2602776 8/1976 Fed. Rep. of Germany ...... 260/348.25

*Primary Examiner*—Norma S. Milestone
*Attorney, Agent, or Firm*—Larson, Taylor, and Hinds

[57] ABSTRACT

Epoxidation of an alkene by reaction with a peroxycarboxylic acid to produce an oxirane. A peroxycarboxylic acid in organic solution is reacted with an alkene to produce a product mixture. Unreacted alkene is separated from the product mixture as a gas. The separated alkene is absorbed into the organic solution containing the peroxycarboxylic acid. The oxirane product is obtained by purification of the product mixture after the alkene has been separated. The organic solution containing the peroxycarboxylic acid is preferably obtained by countercurrently contacting an aqueous phase which includes sulfuric acid, hydrogen peroxide and water and an organic phase containing carboxylic acid and organic solvent.

10 Claims, 1 Drawing Figure

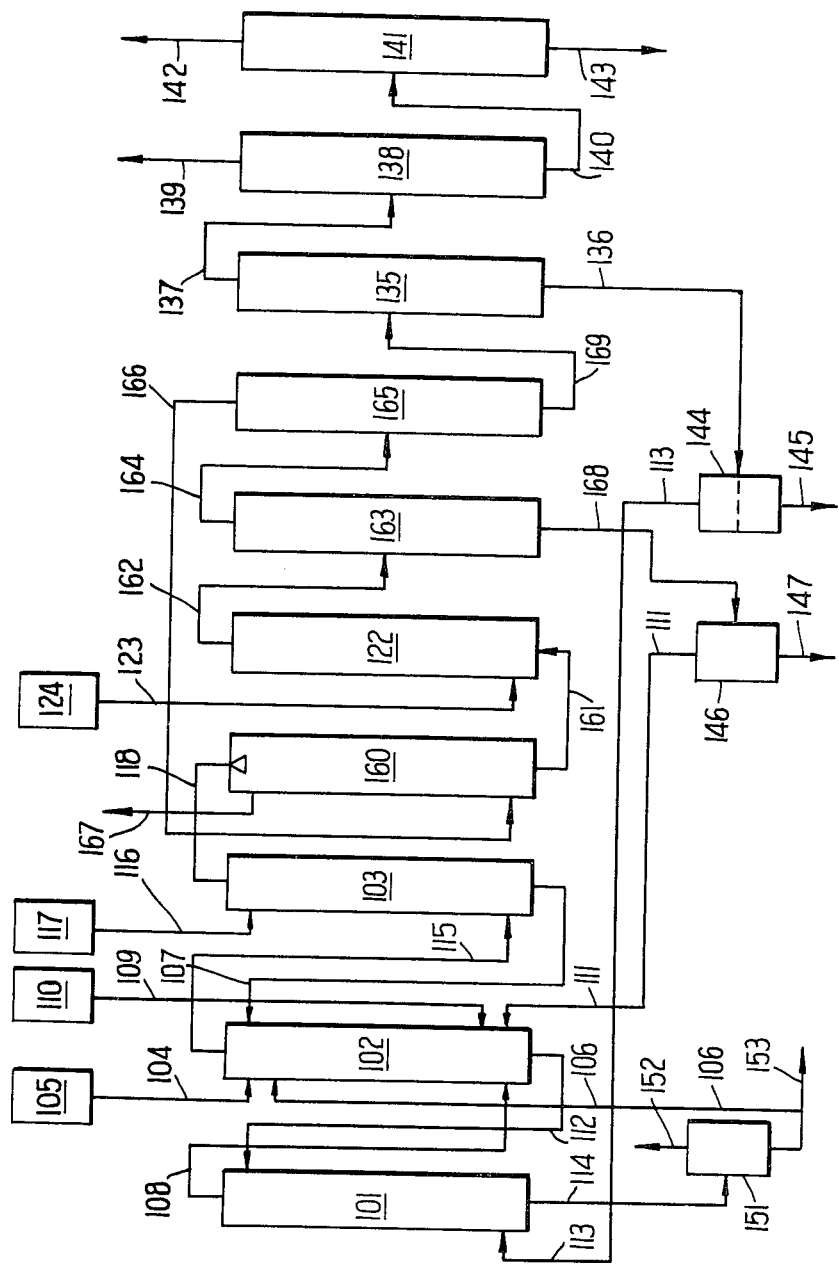

EPOXIDATION

BACKGROUND OF THE INVENTION

The present invention relates to the preparation of peracids (by which we mean herein peroxycarboxylic acids) and the use of such peracids in the epoxidation of alkenes, especially lower alkenes.

DESCRIPTION OF THE PRIOR ART

The general preparation of peracids by the reaction of a carboxylic acid with hydrogen peroxide in an aqueous medium is well known. It is also known that such peracids can be extracted into organic solvents. Finally it is known that peracids can be used to make oxiranes. One process for the preparation of peracids and their use to make oxiranes is disclosed in DOS No. 26 02 776

SUMMARY OF THE INVENTION

It is an object of the present invention to provide a novel continuous process for the epoxidation of an alkene.

Accordingly the present invention provides a continuous process for the epoxidation of an alkene by reaction with a peracid to produce an oxirane, comprising
 (i) preparing a peracid in organic solution;
 (ii) reacting at least a portion of such peracid with an alkene to produce a product mixture;
 (iii) distilling said product mixture such that unreacted alkene is separated therefrom in gaseous form;
 (iv) absorbing the gaseous alkene in the organic solution of step (i); and
 (v) purifying the product mixture, after removal of the alkene, to produce the oxirane.

Conveniently the peracid is formed by reaction between a solution of a carboxylic acid and hydrogen peroxide. Very desirably, for reasons which will appear hereinafter, the said reaction is carried out using countercurrent techniques with the carboxylic acid in organic solution. Moreover desirably reactants not consumed and reaction products, other than the oxirane, are recycled.

More specifically therefore the invention provides a continuous process for the epoxidation of an alkene by reaction with a peracid to produce an oxirane, comprising the cyclic steps of:
 (a) providing an aqueous phase comprising sulphuric acid, hydrogen peroxide and water;
 (b) providing an organic phase comprising a carboxylic acid and an organic solvent;
 (c) contacting said aqueous and organic phases countercurrently to produce an aqueous solution comprising sulphuric acid and water and an organic solution comprising peracid and organic solvent;
 (d) utilising at least a portion of said aqueous solution to provide at least a portion of the aqueous phase of step (a);
 (e) reacting at least a portion of the peracid of said organic solution and an alkene to produce a product mixture comprising oxirane, unreacted alkene, carboxylic acid and organic solvent;
 (f) distilling said product mixture such that unreacted alkene is separated therefrom in gaseous form;
 (g) absorbing the gaseous alkene in the organic solution comprising peroxycarboxylic acid and organic solvent from step (c);
 (h) effecting distillation of said product mixture after removal of the unreacted alkene to produce a product phase comprising the oxirane and a recycle phase comprising carboxylic acid and organic solvent; and
 (i) utilising at least a portion of said recycle phase to form at least a portion of the organic phase of step (b).

Further and subsidiary objects of the invention will appear hereinafter.

It should be noted that the product of an epoxidation reaction is called an "oxirane" or "epoxide", which terms are synonymous.

SELECTION OF THE CARBOXYLIC ACID

As used herein, the term "carboxylic acid" has its normal meaning but it is necessary to emphasise that in practising the invention a proper selection of the "carboxylic acid", "organic solvent" and "alkene" is desirable in order to provide optimum efficiencies. However with the guide lines given herein such selection is within the ability of one skilled in the art.

As will be understood from the statement of the invention given above, the carboxylic acid is caused to react with hydrogen peroxide to give a peracid which then reacts with the alkene to give an oxirane and regenerate the carboxylic acid. It is therefore necessary to select a carboxylic acid such that it and the peracid are sufficiently soluble in water to permit the reaction to take place and also to be soluble in the organic solvent. Moreover the carboxylic acid and peracid should not undergo undesirable side reactions and, for example, should not unduly catalyse ring splitting of the oxirane. For these reasons we prefer to use unsubstituted monocarboxylic acids having at least two but less than six carbon atoms. Within these guide lines substituted, e.g. halogen-substituted, carboxylic acids such as beta-chloropropionic acid may be used, but the strength of such acids and the possibility of their reaction or introduction of chloride species may render them less desirable. Di- and polycarboxylic acids seem to offer no advantages, and may be undesirable since a product mixture containing them cannot readily be distilled to produce the recycle phase without substantial degradation.

The preferred carboxylic acids are therefore acetic and propionic acid.

SELECTION OF THE SOLVENT

As to the organic solvent, its prime function is to set up a discrete organic phase in which the carboxylic acid and peracid are soluble. There are additional criteria for selecting the organic solvent in addition to its solvent powers, namely a low solvent power for water, a low solubility in aqueous sulphuric acid, non-reactivity under the conditions of the reaction in the presence of the other reactants. However in practice one of the most important criteria is the ease with which the solvent can be separated from the product and by-products, preferably by distillation. It is however important to note that it need not be separable from the carboxylic acid and peracids. It will be understood that although various solvents are listed herein, the selection of a solvent for practical use must depend on the precise process and reactants.

The solvent may be a halogenated, e.g. fluorinated or chlorinated, aliphatic hydrocarbon for example: dichloromethane, trichloromethane, tetrachloromethane, chloroethane, 1,1-dichloroethane, 1,2-dichloroethane, 1,1,1-trichloroethane, 1,1,2-trichloroethane, 1,1,1,2-tetrachloroethane, 1,1,2,2-tetrachloroethane, 1-chloropropane, 2-chloropropane, 1,1-dichloropropane, 1,2-dichloropropane, 1,3-dichloropropane, 2,2-dichloropropane, 1,1,1-trichloropropane, 1,1,2-trichloropropane, 1,1,3-trichloropropane, 1,2,2-trichloropropane, 1,2,3-trichloropropane, tetrachloropropanes, or chloro-substituted butanes, pentanes or hexanes.

The solvent may be chlorinated aromatic or cycloaliphatic hydrocarbon, for example: chlorobenzene, cyclohexylchloride.

Chlorinated hydrocarbons, although normally considered very inert, may give rise to chloride species, which in the presence of water and/or sulphuric acid can be very corrosive. It may therefore be desirable to select the solvent from among non-chlorinated hydrocarbons, such as aliphatic hydrocarbons, cycloaliphatic hydrocarbons, aromatic hydrocarbons and alkylaryl hydrocarbons for example: decane, heptane, cyclohexane, benzene, toluene, xylene.

Other solvents, known generally in the art of peracids may be used, such as: esters, for example, ethyl acetate, diethyl phthalate, di-n-butyl phthalate, ethyl propionate nitro compounds, for example, nitrobenzene, benzonitrile ethers for example di-ni-propyl ether.

A solvent mixture can be used, for example that known as petroleum ether which is a mixture of aliphatic hydrocarbons.

It is not theoretically necessary that the organic solvent should be a saturated compound provided that any unsaturation is not epoxidisable under the conditions of the process.

Of all the solvents listed herein, the most preferred is propylene dichloride.

PRODUCTION OF THE PERACID

It is now convenient to develop, in general terms, steps (a) through (d) of the invention as defined generally.

A liquid/liquid contacting device is used and this may comprise any of these devices known in the art arranged to operate in countercurrent. Specific examples are columns, including sieve plate, bubble-cap, stirred and pulsed columns, and a countercurrent series of mixer settlers or any combination. To this contacting device is passed an aqueous phase comprising sulphuric acid, hydrogen peroxide and water and an organic phase comprising carboxylic acid and organic solvent.

Thus in effecting the instant process, the components will partition between the two phases and, in the aqueous phase, the reaction of hydrogen peroxide with carboxylic acid to give peracid will be catalysed by the sulphuric acid. This reaction is normally slow to reach equilibrium but is accelerated by the extraction of the peracid into the organic phase. Indeed operating the contacting device in countercurrent enables better than 90% conversion of the hydrogen peroxide into peracid to be obtained. The process is therefore clearly and surprisingly more efficient in terms of total conversion and conversion per pass than the process of effecting the reaction in the aqueous phase, allowing the aqueous reaction mixture to reach equilibrium and then extracting the equilibrium mixture with a solvent.

Furthermore, operation in countercurrent effectively limits the maximum concentrations of the organic reactants in the aqueous phase so that any risk of explosion is minimised, operation of the known two stage process being known to be potentially hazardous.

In addition to its function as catalyst, the sulphuric acid also has the function of adjusting the specific gravity of the aqueous phase to assist separation of the phases. The relative specific gravities of the organic and aqueous phases will determine their direction of movement in countercurrent operation in a column. However care should be taken, as is known, that the concentration of the sulphuric acid is maintained so as to be sufficient for catalysis but insufficient to cause degradation of any of the organic components by dehydration, etc.

The aqueous solution removed from the contacting device has, in effect, had some or all of its hydrogen peroxide replaced by water. It is therefore desirably concentrated by the removal of water and recycled after addition of hydrogen peroxide.

It is worth commenting that although the theoretical ratio of hydrogen peroxide to carboxylic acid is 1:1 by moles, it is often desirable in chemical operations to have an excess of one reactant. Preferably the instant reaction is effected with an excess of carboxylic acid to ensure maximum reaction of hydrogen peroxide and so avoid the known problems of effectively recovering the hydrogen peroxide from the aqueous solution being concentrated.

THE EPOXIDATION REACTION

Turning now to steps (e) and (f) of the invention as stated, the organic solution of peracid is reacted, without prior separation of peracid, with an alkene to give an oxirane.

SELECTION OF THE ALKENE

The term "alkene" is used herein to mean an epoxidisable compound containing an olefinic double bond, i.e. the group $>C=C<$. The term includes di- or polyunsaturated and/or substituted compounds where such di- or polyunsaturation and/or substitution will not prevent epoxidation.

Although the present invention can be applied to ethylene, the lowest alkene, it is not thought that the reaction would be economically attractive at the present time as compared with the direct oxidation of ethylene. However it might be economically suitable for substituted ethylenes, e.g. phenylethylene (i.e. styrene). It would appear that the invention is likely to prove most advantageous when applied to propylene. Propylene is otherwise known as propene.

The invention also appears to be economically attractive when applied to butenes, to the various pentenes and to higher alkenes such as octene, decene, tetradecene, hexadecene, octadecene, dodecene and eicosene.

Cyclic alkenes can also be used such as cyclopentene, cyclohexene and alkyl cyclohexenes.

Such polyunsaturated compounds as butadiene, pentadiene, hexadiene, vinyl cyclohexene and polybutadiene can also be used.

Where appropriate, the term "alkene" is intended to include both straight and branched chain isomers and internal and external olefins. It also includes substituted derivatives, e.g. chloro- and hydroxyl- substituents, provided that the substitution does not hinder the epoxidation reaction.

In addition to substituted alkenes as normally understood, the invention can be applied to ethers, esters, ketones etc., containing an olefinic double bond but it will be realised that additional oxidation reactions may take place.

It will be observed that by using an organic solution of the peracid, water and sulphuric acid are not brought into contact with the oxirane so ring opening is reduced. If desired, the organic solution from step (c) can be dried before step (e), as by distillation to remove water, conveniently as an azeotrope. Moreover if carry over of acidic species is a disadvantage for this or other reasons, the organic solution of peracid may be washed with a small amount of water in substitution for or in addition to drying. If necessary microfiltration or other similar techniques can be used to remove entrained water.

PRODUCTION OF PERACID—GENERAL CONDITIONS

Dealing with this part of the process of this invention in more detail and as applied specifically to the preparation and use of perpropionic acid, using propylene dichloride as the oganic solvent, an aqueous phase is supplied to the extraction device, e.g. the upper part of an extraction column, to pass downwardly therethrough. This aqueous phase comprises sulphuric acid, hydrogen peroxide and water. The proportion of sulphuric acid is preferably approximately 40% by weight and is desirably between 30% and 60% by weight. If a lower yield is acceptable then the proportion of sulphuric acid can be between 15% and 85%. Conveniently however for operating reasons the sulphuric acid is derived from 75% by weight sulphuric acid solution in water which forms a feedback from the purification stages which will be described hereinafter, together with make-up acid. It should be recalled that the specific gravity of the aqueous phase will depend largely on the concentration of sulphuric acid.

The hydrogen peroxide is conveniently approximately 29% by weight of the aqueous phase and in practice between 10% and 35% is very satisfactory. If lower yields are acceptable, then as little as 5% could be used, but above about 35% the mixture could be hazardous. This hydrogen peroxide is very conveniently supplied as approximately 70% by weight solution in water.

Water makes up the third component of the aqueous phase and its proportions can readily be found by difference.

The organic phase is fed into the lower part of the extraction column to pass upwardly in countercurrent with the aqueous phase and comprises, for the production of perpropionic acid, a solution of propionic acid in an organic solvent such as propylene dichloride. The concentration of the proponic acid is desirably 20% or preferably between 15% and 30% of the organic phase or conveniently between 10% and 50% by weight.

The relative volumes of the aqueous and organic phases and their concentrations together set the ratio between hydrogen peroxide and propionic acid. This ratio is theoretically 1:1 by moles but is conveniently 1:1.4 and may be from 1:0.5 to 1:4, or, if low conversions are acceptable, from 1:0.1 to 1:10. However if an excess of hydrogen peroxide is used, it will appear in the effluent from the extraction column and this may be undesirable; the mole ratio is therefore preferably 1:>1.

The function of the organic solvent is to extract the perpropionic acid from the aqueous phase in which it is formed by reaction between the hydrogen peroxide and propionic acid extracted from the organic phase into the aqueous phase. The effect of this is to shift the equilibrium in a favour of formation of perpropionic acid. Thus in a two stage process in which the propionic acid is reacted in an aqueous system with hydrogen peroxide and the resultant peracid extracted into an organic solvent all under optimum conditions, it is only possible to achieve about 66% conversion of propionic acid or hydrogen peroxide to perpropionic acid. However using the process of this invention, over 90% conversion of hydrogen peroxide to perpropionic acid can be obtained. In consequence the process of this invention is very much more efficient and therefore more effective in terms of plant utilisation.

It may be convenient to carry out a further extraction of the aqueous phase leaving the base of the extraction column using fresh organic solvent in order to extract substantially all of both propionic acid and perpropionic acid from the aqueous effluent. It will be understood that in accordance with known extraction techniques, this further extraction can in fact be carried out in the same extraction column. It may also be convenient to use the upper part of the extraction column, or a separate column, to effect a back-wash operation on the organic phase in order to remove dissolved hydrogen peroxide. This can be effected by dividing the aqueous feed to the column into two portions, one being primarily dilute sulphuric acid and the other primarily hydrogen peroxide, and introducing these two portions at spaced locations in the column.

Two side reactions could in theory occur in the extraction column, namely the reaction of hydrogen peroxide with sulphuric acid to form Caro's acid and the reaction of propionic acid with perpropionic acid to give propionyl peroxide. However the simultaneous extraction into the organic phase has the general effect of minimising these side reactions as compared with the two stage process and the process is also much safer than the said two stage process which is subject to an explosion hazard.

The reaction proceeds naturally at a satisfactory rate so that operation at natural temperatures is satisfactory. Natural temperature is to some extent dependent on a scale effect since only little heat is evolved on mixing and reaction. Since the reaction is not markedly temperature sensitive no special steps are needed and a column temperature of 20°–25° C. is satisfactory.

In selecting the various reactants for the production of the peracid, it is necessary to remember that the reaction system is dynamic rather than static. In consequence although individual parameters can be measured in static conditions, the dynamic interactions cause considerable differences.

As a guide to the selection of a reactant/solvent system for the production of the peracid, reference should be made to Table I which shows some relevant data.

TABLE I

| | $pK \times 10^5$ | Boiling point °C. | Density | Solubility in water |
|---|---|---|---|---|
| Carboxylic acids | | | | |
| formic | 17.7 | 101 | 1.22 | ∞ |
| acetic | 1.8 | 118 | 1.04 | ∞ |
| propionic | 1.3 | 141 | 0.99 | ∞ |
| n.butyric | 1.5 | 163 | 0.96 | ∞ |
| caproic | 1.4 | 205 | 0.93 | ∂ |
| n.heptoic | 1.3 | 223 | 0.92 | ∂ |
| chloracetic | 140 | 189 | 1.28 | v |
| αchloropropionic | 147 | 186 | 1.28 | ∞ |
| β-chloropropionic | 10 | 204 | — | s |
| Solvents | | | | |
| chloroethane | | 13.1 | 0.90 | ∂ |
| tetrachloroethane | | 146 | 1.60 | ∂ |
| propylene dichloride | | 96 | 1.16 | ∂ |
| chlorobenzene | | 132 | 1.11 | i |

TABLE I-continued

| | pK × 10⁵ | Boiling point °C. | Density | Solubility in water |
|---|---|---|---|---|
| cyclohexylchloride | | 142 | 100 | i |
| trichloroethylene | | 87 | 1.462 | ∂ |
| tetrachlorethylene | | 121 | 1.623 | i |
| decane | | 174 | 0.73 | i |
| heptane | | 98 | 0.68 | i |
| cyclohexane | | 81 | 0.78 | i |
| benzene | | 80.1 | 0.88 | ∂ |
| toluene | | 110 | 0.87 | i |
| ethylacetate | | 77 | 0.90 | s |
| ethyl propionate | | 99 | 0.89 | ∂ |
| nitrobenzene | | 211 | 1.20 | ∂ |
| di n-propyl ether | | 91 | 0.74 | ∂ |
| petroleum ether | | 80-100 | 0.8 | i |

Notes to Table I
(1) The pK figures are for aqueous solution at 25° C.
(2) The symbols for solubility are taken from Handbook of Chemistry and Physics; The chemical Rubber Co.; 46th Ed.

EPOXIDATION—GENERAL CONDITIONS

The solution of peracid in organic solvent is used in step (e) of the invention.

In order to effect the actual epoxidation reaction, the solution of perpropionic acid in organic solvent from the extraction column is mixed with a molar excess, conveniently of the order of 25% to 50% (although it could be lower or higher) or alkene, e.g. propene, and is then pumped to a suitable reactor, e.g. a pressurised water-cooled tubular reactor.

Temperatures in the range 50°-150° C. can be used, but we prefer to operate in the range 75°-120° C. and desirably in the range 90°-110° C. The degree of cooling is desirably adjusted so as to provide this preferred temperature. The pressurisation is sufficient to maintain the propene in solution at the chosen temperature. If an adequate residence time is allowed in this reactor, for example in excess of 20 minutes and conveniently about 25 minutes in the manufacture of propylene oxide, but depending on temperature, very nearly complete conversion of the perpropionic acid will be achieved. Thus approximately 99% of the perpropionic acid can be caused to react. Moreover the reaction is very selective and of the perpropionic acid which does react, in excess of 98% reacts to give propylene oxide and less than 2% to give by-products. Of the side reactions which take place, the most common are the degradation of perpropionic acid into propionic acid and oxygen or into ethanol and carbon dioxide. There is in addition some formation of acetaldehyde, propionaldehyde, propylene glycol or propylene glycol esters and other side products.

The precise physical form of the reactor is not important and we visualise that cocurrent tubular reactors and continuous stirred tanks can both be used, either individually or in some combination. Multi-stage batch reactors can also be used.

SEPARATION OF ALKENE

It will be apparent that, in view of the molar excess of alkene, some alkene will remain unreacted. In accordance with step (f) of the invention as described in general terms, the unreacted alkene is separated from the product mixture. This separation is most conveniently effected by a distillation operation which, in the case of propylene, is simply conducted by reducing the pressure to atmospheric. It should be pointed out that in selecting the reactants, solvent etc. the need for this separation should be borne in mind.

Rather than merely condensing the separated alkene, it is desirably condensed by contact with a cooled solution of peracid in organic solvent in which it dissolves, this solution then being used in step (e). Any impurities such as propane will not dissolve and can be separated.

PURIFICATION OF PRODUCT

The product mixture from the reactor comprises oxirane, carboxylic acid and organic solvent and is taken in step (g) to a multi-stage distillation process intended to separate out the pure product, recycle streams and the impurities.

In the production of propylene oxide, using propylene dichloride as the solvent, the following stages of distillation are appropriate.

In the first stage, the light fraction comprises the propylene oxide with low boiling point impurities such as acetaldehyde, water and some propylene dichloride. The heavy fraction from this first stage is propionic acid in propylene dichloride and this is recycled but may be distilled to remove heavy impurities such as propylene glycol. The light fraction from the first stage is re-distilled in a second stage to give a second light fraction comprising the propylene oxide, acetaldehyde and propionaldehyde and a second heavy fraction comprising water and propylene dichloride which is also recycled. Successive further distillations purify the propylene oxide.

RECYCLE

In accordance with step (h) the recycle phase is passed back to the extraction column as the organic phase, after the addition of organic solvent and carboxylic acid in order to make up for the small inevitable wastage and the purges. Conveniently in the case of a propylene oxide/propionic acid/propylene dichloride system, the heavy fraction from the first distillation stage (which comprises propionic acid in propylene dichloride) is used as the main feed of organic phase to the liquid/liquid contacting device and the heavy phase from the second distillation stage (which comprises propylene dichloride) is used to carry out the further extraction of the aqueous phase.

Referring now to the extraction column, it will be recalled that the aqueous phase is supplied to the upper part of the column and is withdrawn from the lower part of the column. As withdrawn from this lower part of the column, the aqueous phase comprises sulphuric acid and water together with perhaps small amounts of hydrogen peroxide, since as explained, the conditions in the extraction column are preferably such as to ensure almost complete reaction of the hydrogen peroxide. It will be recalled that the second extraction will have removed substantially all the propionic and perpropionic acid from the aqueous effluent. The dilute sulphuric acid is preferably concentrated, desirably by evaporation or distillation, in order to remove the unwanted water and then is recycled to the extraction column, in accordance with step (d).

MODIFICATIONS

The modifications necessary to convert the above generalised description relating to propylene to a description relating to any alkene will be apparent to one skilled in the art. However in order to assist in the selection of suitable carboxylic acids and organic solvents for any given alkene reference may conveniently be made to Table II hereof.

TABLE II

| | Boiling point | Density |
|---|---|---|
| Alkenes | | |
| allyl chloride | 45 | 0.94 |
| butylene | −6.3 | 0.59 |
| decane | 170 | 0.74 |
| propylene | −47.8 | — |
| styrene | 145 | 0.91 |
| Epoxides | | |
| epoxy-butane | 61 | 0.84 |
| epoxy-decane | 219 | — |
| epoxy-propane | 35 | 0.86 |
| styrene oxide | 191 | 1.05 |
| epichlorhydrin | 1166 | 1.18 |
| By-products | | |
| acetaldehyde | 20.8 | 0.78 |
| ethanol | 78.5 | 0.79 |
| propionaldehyde | 48.8 | 0.81 |
| propylene glycol | 189 | 1.04 |
| propylene dipropionate | 200 | |

For any solvent/carboxylic acid/alkene combination the optimum working conditions (e.g. temperatures and concentrations) may be determined by trail and experiment (or predicted from the conditions which obtain in laboratory experiments with batch processes). One factor which can be determined from bath processes is the distribution coefficient between the organic and aqueous phases for the species in question. Of course, this is only a guide, for kinetic as well as (indeed rather than) thermodynamic factors are involved. If with any solvent the resulting concentration of peracid in the organic solution is inconveniently low for a particular purpose, it may be desirable to concentrate the solution, e.g. by distillation under reduced pressure.

DESCRIPTION OF PREFERRED EMBODIMENT

In order that the invention may more readily be understood one embodiment of the same will now be described by way of example and with reference to the accompanying drawing which is a flow sheet for the production of propylene oxide.

The present invention, being a continuous process, is best described with reference to the concentration of reactants flowing in various parts of the system. The figures given correspond to a pilot scale operation but it will be readily understood by those skilled in the art how to scale up to any desired degree.

The drawing illustrates a plant for the production of propylene oxide in accordance with the invention, using propionic acid as the carboxylic acid and propylene dichloride as the solvent. It will be seen that the plant has three series-connected stages of countercurrent extraction and four series-connected stages of distillation in the purification train. It will be understood that in a practical plant, two or more of these series-connected stages may be combined in a single column. However for the sake of clarity they are illustrated as separate stages.

The extraction section which also includes the reaction section comprises columns 101, 102 and 103 all arranged to operate in countercurrent. Step (c) of the present invention takes place mainly in the column 102, which is the main reaction column. To that end hydrogen peroxide is supplied to the head of the column 102 by a line 104 from a storage tank 105. Aqueous sulphuric acid is supplied to the head of the column 102 by a line 106 and in accordance with step (d) of the invention this is a recycle phase. Aqueous sulphuric acid is also supplied to the head of the column 102 by a line 107 taken from the base of the column 103. The hydrogen peroxide, sulphuric acid and water supplied by the lines 104, 106 and 107 together constitute the aqueous phase of step (a). An organic solution is supplied to the base of the column 102 by a line 108 from the head of the column 101. Fresh propionic acid in propylene dichloride from a make-up storage tank 110 is also supplied to the base of the column 102 by a line 109. Finally a recycle phase comprising propionic acid in propylene dichloride in accordance with step (h) is supplied to the base of the column 102 by a line 111. The carboxylic acid and organic solvent provided by the lines 108, 109 and 111 to the base of the columnn 102 together constitute the organic phase in accordance with step (b). Since the organic phase is lighter than the aqueous phase, these will pass in countercurrent through the column 102 in accordance with step (c) and will react in order to produce perpropionic acid.

Thus an aqueous solution comprising sulphuric acid and water is taken from the base of the column 102 by a line 112 and is taken to the head of the column 101 which functions as an organic back-wash column. Solvent, substantially free of propionic acid, is supplied to the base of the back-wash column 101 by a line 113 and passes in countercurrent to the aqueous solution in order to back-wash it and strip from it as much propionic acid as possible. The conditions are such that the aqueous effluent from the back-wash column 101 which is taken from the base by line 114 contains substantially no carboxylic acid, peracid or hydrogen peroxide. The organic solution from the head of the column 102 commrises a solution of perpropionic acid in propylene dichloride and is taken by a line 115 to the base of the column 103 which acts as an aqueous back-wash column. To that end, the head of the column 103 is provided with fresh sulphuric acid in aqueous solution by a line 116 from a make-up tank 117, this sulphuric acid passing out of the column 103 by the line 107. The function of this aqueous acid back-wash is to strip the organic phase flowing through the column 103 and remove from it as much of the dissolved hydrogen peroxide as possible.

The organic solution leaves the head of the acid back-wash column 103 by a line 118 and is taken to a multi-plate contactor column 160 operating at −5° C., where, as explained later, it contacts unreacted propylene and dissolves it. The organic solution leaves the base of the contactor column 160 by a line 161 and is taken to a reactor 122 which is conveniently illustrated as a column, although in practice a long tubular reactor would be preferred. Propylene is also fed to this reactor by a line 123 from a storage vessel 124. It will be appreciated that under normal conditions of temperature and pressure, propylene is a gas and therefore the reactor 122 is operated under pressure in order that the propylene should be kept in solution in the organic solution. The propylene reacts with the perpropionic acid in the reactor 122 to give propylene oxide and propionic acid in accordance with step (e). This product mixture is taken by a line 162 to a first distillation column 163 and in this column all except a solution of propionic acid in propylene dichloride is distilled off as a light fraction. This light fraction is taken by a line 164 to a condenser 165 where it is cooled sufficiently for all except the propylene and propane to condense. This gas is taken by a line 166 from the condenser 165 back to the contactor 160 where the propylene is absorbed. Any propane is not absorbed and is passed out of the contactor 160 to waste by a line 167.

The heavy fraction leaves the distillation column 163 by a line 168. The condensate in the condenser 165 is taken by a line 169 to a second distillation column 135. The heavy fraction from the distillation column 135 is taken by a line 136 and comprises essentially propylene dichloride without any substantial amount of dissolved propionic acid. The light fraction is taken by a line 137 to a third distillation column 138. This feed comprises substantially pure propylene oxide, that is to say propylene oxide which has had unreacted propylene, propylene dichloride and propionic acid removed from it. It now undergoes a first distillation stage of purification in the column 138, the low boiling impurities being withdrawn and passed to waste through a line 139. The heavy fraction is taken by a line 140 to the second purification stage constituted by the fourth distillation column 141 where the light fraction constitutes the product and is withdrawn through a line 142 whilst the high boiling impurities are passed to waste through a line 143.

As will be apparent there are a number of recycle streams and reactant purification is conveniently effected on the recycle streams. Thus the line 136 from the column 135 carries propylene dichloride together with any water which has passed out of the column 103 or has been produced subsequently. Although the recycle stream can tolerate a reasonable amount of water, it is desirable to remove any excess water and the line 136 therefore leads to a decanter 144 where this recycle stream is permitted to separate into two phases and the lower phase, being chiefly water, is discarded to waste through a line 145. The propylene dichloride is taken from the decanter 144 by the line 113 previously referred to.

The stream in the line 168 comprises essentially propionic acid in propylene dichloride and this is to be recycled in accordance with step (h). However, since some degradation products will collect in this stream, the line 168 leads to a distillation column 146 from which the light fraction is taken by the line 111 previously referred to. The heavy fraction is discarded to waste through a line 147.

The aqueous solution taken from the base of the organic back-wash column 101 by the line 114 is to be utilised at least in part, in accordance with step (d) but it will be appreciated that this aqueous solution contains too much water for direct replacement as step (a) since the original hydrogen peroxide content has reacted to give water. The line 114 therefore leads to a distillation column 151 where it is distilled in order to provide a light fraction which is substantially water and which is taken off by a line 152 and passed to waste. The heavy fraction from the column 151 comprises sulphuric acid in water and could conveniently be re-distilled in order to remove heavy boiling impurities which would otherwise accumulate in the aqueous phase. However in the preferred arrangement a bleed from the aqueous phase is taken from the heavy fraction from the distillation column 151 by a line 153 and the remainder is passed back by the line 106 to the top of the column 102.

The columns 101, 102 and 103 preferably operate at normal temperature, that is to say without any added heating or cooling, and under normal hydrostatic pressure. The reactor 122 conveniently operates at 90°–110° C. and under a pressure of 12 atm. in order to keep the propylene in solution. The first distillation column 163 can conveniently operate at normal pressure, the product mixture temperature of about 100° C. being sufficient to cause flash distillation of all except propionic acid in propylene dichloride. The condenser column 165 conveniently operates at normal temperatures and an over pressure of 0.25 kg/cm$^2$ so that all except the propylene and propane is condensed. The second, third and fourth distillation columns 135, 138 and 141 all operate at about atmospheric pressure and with head temperatures of about 35° C. The column 135 has a bottom temperature of about 72° C. so that only the propylene dichloride is not distilled off. The column 138 has a bottom temperature of 40° C. so that the propylene oxide is not distilled of whilst the column 141 has a bottom temperature of 50° C. to separate propylene oxide and propionaldehyde. The columns 146 and 151 operating in the recycle streams can conveniently operate at temperatures and pressures of 80° C./1 atm. and 130° C./100 torr. respectively.

It will be apparent that in order to operate the present invention as described it is necessary to be able to separate unreacted alkene from the reaction product mixture. This is most conveniently done by distillation and it is therefore desirable that the alkene should be the lowest boiling major component of the reaction product mixture. The carboxylic acid and solvent should be chosen accordingly.

We claim:
1. A continuous process for the epoxidation of an alkene by reaction with a peroxycarboxylic acid to produce an oxirane, comprising:
   (i) preparing a solution comprising peroxycarboxylic acid and organic solvent;
   (ii) mixing an alkene and said solution comprising peroxycarboxylic acid and organic solvent;
   (iii) reacting said peroxycarboxylic acid and said alkene to produce a product mixture;
   (iv) distilling said product mixture such that unreacted alkene is separated therefrom in gaseous form;
   (v) absorbing said gaseous alkene in said solution comprising peroxycarboxylic acid and organic solvent before step (ii); and
   (vi) purifying the product mixture, after removal of the alkene, to produce the oxirane.

2. The process of claim 1, wherein the peroxycarboxylic acid is produced by reaction between a carboxylic acid and hydrogen peroxide.

3. The process of claim 2, wherein the carboxylic acid is in organic solution and the hydrogen peroxide is in aqueous solution and the reaction is carried out using countercurrent techniques.

4. A continuous process for the epoxidation of an alkene comprising the cyclic steps of:
   (a) providing an aqueous phase comprising sulphuric acid, hydrogen peroxide and water;
   (b) providing an organic phase comprising a carboxylic acid and an organic solvent;
   (c) contacting said aqueous and organic phases countercurrently to produce an aqueous solution comprising sulphuric acid and water and an organic solution comprising peroxycarboxylic acid and organic solvent;
   (d) utilising at least a portion of said aqueous solution to provide at least a portion of the aqueous phase of step (a);

(e) mixing an alkene and said organic solution comprising peroxycarboxylic acid and organic solvent;

(f) reacting said peroxycarboxylic acid of said organic solution and said alkene to produce a product mixture comprising oxirane, unreacted alkene, carboxylic acid and organic solvent;

(g) distilling said product mixture such that unreacted alkene is separated therefrom in gaseous form;

(h) absorbing the gaseous alkene in the organic solution comprising peroxycarboxylic acid and organic solvent before step (e);

(i) effecting distillation of said product mixture after removal of the unreacted alkene to produce a product phase comprising the oxirane and a recycle phase comprising carboxylic acid and organic solvent, and (j) utilising at least a portion of said recycle phase to form at least a portion of the organic phase of step (b).

5. The process of claim 4, wherein the organic solution comprising peroxycarboxylic acid and organic solvent used in step (h) is cooled.

6. The process of claim 4, wherein the alkene is in stoichiometric excess.

7. The process of claim 4, wherein the organic solvent is a chlorinated hydrocarbon.

8. The process of claim 4, wherein the organic solvent is benzene.

9. The process of claim 4, wherein the aqueous solution is concentrated by the removal of water prior to being used as a portion of the aqueous phase.

10. The process of claim 4, wherein the carboxylic acid is an unsubstituted monocarboxylic acid having from 2 to 6 carbon atoms.

* * * * *